United States Patent [19]

Alvarez

[11] 4,327,083

[45] Apr. 27, 1982

[54] TREATMENT OF HYPERTENSION WITH BISULFITE

[75] Inventor: Jose A. A. Alvarez, Mexico City, Mexico

[73] Assignee: T & R Chemicals, Inc., Clint, Tex.

[21] Appl. No.: 75,423

[22] Filed: Sep. 14, 1979

Related U.S. Application Data

[63] Continuation-in-part of Ser. No. 859,705, Dec. 12, 1977, abandoned.

[51] Int. Cl.$^3$ .............................................. A31K 33/04
[52] U.S. Cl. ................................................... 424/162
[58] Field of Search ............................... 424/162, 325

[56] References Cited

U.S. PATENT DOCUMENTS 3,836,639  9/1974  Teler et al. ........................... 424/101

OTHER PUBLICATIONS

Rost et al., Arb. A. D. Kaiserlichen Gesundheitsamte, vol. 21, 1904, pp. 187–303 & 312–371.
CA 42, 2355$^{g-h}$ (1948).
CA 43, 1861$^9$ (1949).
Kikugawa et al., J. Pharm. Sci., (1972) 61(12) pp. 1904–1907.
CA 9th Coll. Ind. 37336 CS and vol. 82, 107247f.
CA 85, 91235z (1976).
CA 7, 1551 (1913).
CA 20, 4103 (1932).

Primary Examiner—Frank Cacciapaglia, Jr.
Attorney, Agent, or Firm—Hill, Van Santen, Steadman, Chiara & Simpson

[57] ABSTRACT

Improvement in hypertension in man is achieved through the use of sodium bisulfite.

2 Claims, No Drawings

TREATMENT OF HYPERTENSION WITH BISULFITE

RELATED APPLICATION

This application is a continuation-in-part of my co-pending earlier filed U.S. patent application Ser. No. 859,705, filed Dec. 12, 1977, but now abandoned, the disclosure and contents of which are entirely incorporated herein by reference.

BACKGROUND OF THE INVENTION

Sodium bisulfite (usually shown by formula to be $NaHSO_3$) has heretofore been used for many commercial purposes, such as a preservative for prevention of the deterioration of liquids, such as food stuffs and pharmaceutical solids, and has been used medically externally for parasitic skin diseases and internally as a gastrointestinal antiseptic. So far as now known, sodium bisulfite has never previously been used by man at low dosage rates on a generally regular basis over an extended period of time.

The sodium bisulfite of commerce consists chiefly of sodium metabisulfite, $Na_2S_2O_5$, and for purposes of this invention such is believed to possess the same properties as (and to be equivalent to) the true sodium bisulfite when dissolved in an aqueous solution.

BRIEF SUMMARY OF THE INVENTION

It has now been discovered that sodium bisulfite is useful in low doses and over extended periods in the treatment and prevention of cardiovascular diseases, such as atherosclerosis, hypertension, and the like, when consumed orally by humans in an aqueous dilute solution.

Such dilute sodium bisulfite solutions can be used before, during, or after the onset of a cardiovascular disease with beneficial results. Even when used on patients who might be considered terminally affected by such a degenerative condition, beneficial results are observed.

Sodium bisulfite has been found to be effective when given in an aqueous dilute solution at dose rates ranging from about 0.2 to 2 mgm per kilogram of body weight, though it is believed that larger and/or smaller doses can be used without departing from the spirit and scope of the present discovery. One dose rate, for example, which has usually been found to be particularly effective for man varies from about 50 to 75 mgm per day per average human adult patient (e.g. about 70 kg) of sodium bisulfite taken orally as a dilute aqueous solution of from about 1 to 5 percent by weight in distilled water and ingested before, during or after each of the daily meals, such as breakfast, lunch, and dinner.

In one aspect, use of the present invention leads to symptomatic and objective improvement in a cardiovascular disease condition, such as hypertension in man. By the term "symptomatic improvement", as used herein, reference is had to an improvement in a patient's subjective symptoms as reported by that patient. By the term "objective improvement", as used herein, reference is had to a measurable and objective change in the patient's condition (e.g. blood pressure), from an initial (at the start of treatment) to a subsequent (during or after treatment) condition.

Other and further aspects, objects, purposes, advantages, aims, utilities, features and the like will be apparent to those skilled in the art from a reading of the present specification.

DETAILED DESCRIPTION

More particularly, this invention concerns a process for treating a human wherein there is introduced preferably orally into such a human a pharmaceutically effective amount of sodium bisulfite.

In one preferred mode of using this invention, an aqueous solution of from about 1 to 5% by weight sodium bisulfite is prepared. Then, such solution is orally consumed by a human at the total (or accumulated) dose rate ranging from 0.2 to 2.0 mgm per each kilogram of body weight per day, more preferably in the form of from two to four spaced doses per day, each such dose being preferably taken around meal time. A presently most preferred dose rate comprises one in the range from about 1.0 to 1.4 mgm per kg. of body weight per day taken in the form of at least two spaced oral doses (using an aqueous solution as described herein).

In such mode of using this invention, one achieves symptomatic and even objective improvement in a cardiovascular disease, such as atherosclerosis and hypertension.

The use of this invention is preferably practiced at present using a dilute aqueous solution of sodium bisulfite. Because of the tendency for sodium bisulfite to undergo oxidation when in aqueous solution when oxygen is present, it is presently common and even preferred in using this invention to employ a solution which comprises on a 100 percent by weight total solution basis:

(a) from about 1 to 5 percent by weight of dissolved inorganic solids, and
(b) the balance up to 100 percent by weight of any given solution being water.

In such solution, such dissolved inorganic solids comprise on a calculated 100 percent by weight dry basis:

(a) at least about 50 and more preferably at least 90 percent by weight sodium bisulfite, and
(b) the balance up to 100 percent by weight thereof being inorganic compounds produced or producible by the oxidation of sodium bisulfite.

The water used in such a solution is preferably purified (e.g. filtered, deionized, distilled or the like). After preparation, such a solution is preferably stored in a closed container to reduce oxidation.

Such an aqueous solution can be directly consumed by a patient as drops (e.g. from about 5 to 9 drops per meal, depending upon dose rate for an individual patient) or as a capsule or the like, as desired.

Symptomatic improvement in a patient's condition may occur within two weeks to four months of continuous usage of sodium bisulfite in accord with the teachings of this invention.

Because of the subjective improvement reported by patients suffering from atherosclerosis, it may be that use of this invention exerts a favorable influence on blood lipids, such as a fall in total cholesterol, low density lipoprotein and trylycerides and a rise in high density lipoprotein.

One important advantage of the present invention is the circumstance that the indicated desirable results are achieved with little or no apparent side effects surprisingly.

EMBODIMENTS

The present invention is further illustrated by reference to the following case histories. Those skilled in the art will appreciate that other and further embodiments are obvious and within the spirit and scope of this invention from the teachings of these present examples taken with the accompanying specification.

PREPARATION OF THE SOLUTION

A

A solution of sodium bisulfite is prepared by dissolving pharmaceutical grade (U.S.P. Grade) powdered sodium bisulfite (sodium metabisulfite) in distilled water at room temperature to form a 1 percent by weight aqueous solution.

This solution is then placed into a series of plastic squeeze bottles, each with a volumetric capacity of about 50-52 ml. Each bottle is provided with a cap permitting drop-wise dispensing of solution from such bottle at an estimated rate of 15 drops per ml.

B

A solution of sodium bisulfite is prepared by dissolving pharmaceuticl grade (U.S.P. Grade) powdered sodium bisulfite (sodium metabisulfite) in distilled water at room temperature to form a 2 percent by weight aqueous solution.

This solution is then placed into a series of squeeze bottles, each with a volumetric capacity of about 50-52 ml. Each bottle is provided with a cap permitting drop-wise dispensing of solution from such bottle at an estimated rate of 15 drops per ml.

C

A solution of sodium bisulfite is prepared by dissolving pharmaceutical grade (U.S.P. Grade) powdered sodium bisulfite (sodium metabisulfite) in distilled water at room temperature to form a 2.5 percent by weight aqueous solution.

This solution is then placed into a series of plastic squeeze bottles, each with a volumetric capacity of about 50-52 ml. Each bottle is provided with a cap permitting drop-wise dispensing of solution from such bottle at a rate estimated to be 15 drops per ml.

D

A solution of sodium bisulfite is prepared by dissolving pharmaceutical grade (U.S.P. Grade) powdered sodium bisulfite (sodium metabisulfite) in distilled water at room temperature to form a 5 percent by weight aqueous solution.

This solution is then placed into a series of plastic squeeze bottles, each with a volumetric capacity of about 50-52 ml. Each bottle is provided with a cap permitting drop-wise dispensing of solution from such bottle at an estimated rate of 15 drops per ml.

In each of the following numbered case histories, each patient is provided with such a bottle of solution D, unless otherwise noted, and is instructed to dose himself (or herself, as the case may be) from the bottle so provided at the rate of seven drops to be taken orally with each of his (her) three daily meals. When the contents of one such bottle is thus so gradually consumed by an individual patient, another is provided to him (her).

EXAMPLE 1

A 67 year old man, height 5'6", weight 56.8 kilograms, apparently had generalized poor arterial circulation. He would get cramps in his legs when he stood up for more than half an hour or walked a short distance, and the tips of his fingers had a cyanotic color, especially on cold days. It was felt that he suffered from generalized atherosclerosis. He had also sustained a heart attack about 3 years previously, and was afflicted by a cardiac arrhythmia and hypertension.

After about one month of this continuous dosage with Solution D, this man had improved. No recurrence of his original condition including hypertension was observed after about three years of continuously following this dosage.

EXAMPLE 2

A woman, age 50, height 5'5", weight 53.6 kilograms, had a high level of urea in the blood due apparently to nephrosclerosis. It was felt that she also had hypertension and generalized atherosclerosis.

After about two weeks of treatment with Solution D, she began to experience a remarkable improvement and her blood urea nitrogen level fell to normal. No recurrence of her original symptoms was observed after almost three years of continuous use of this substance.

EXAMPLE 3

A man, age 66, height 5'6", weight 71.8 kilograms, had a severe arterial insufficiency of such degree that one of his toes was to be amputated because of impending gangrene. It was felt that he had atherosclerosis. He also had coronary deficiency and hypotension. He was unable to sleep because of night pain in the foot.

After about 2 weeks of continuous treatment with Solution D, he was sleeping well. Also, the black area on his toe had disappeared. No recurrence of his original symptoms or signs were observed after about $4\frac{1}{2}$ years of continuous use of this solution.

EXAMPLE 4

A woman, age 48, height 5'4", weight 61.3 kilograms, complained of intermittent attacks of intense constricting pain in the chest felt to be angina pectoris due to coronary atherosclerosis and hypertension.

After about two weeks of continuous treatment with Solution D, she began to show a substantial relief from the pain in her chest. Continuance of the treatment resulted in a loss of all her symptoms in about 2 months, and, for about $2\frac{1}{2}$ years, there has been no recurrence of her original symptoms.

EXAMPLE 5

A man, age 32, height 5'10", weight 81.8 kilograms, had a myocardial infarction at the age of 29, and he had been treated with heparin as an anticoagulant and also with vasodilator agents. It was felt that he had coronary atherosclerosis and hypertension. He was also on a special low salt, low fat diet.

This man improved symptomatically (in the patient's estimation) after about 2 weeks of treatment with Solution D. A gradual lowering of his heparin dose was achieved, and also of his vasodilator medicines. With continuance of the treatment, this man has been enjoying good health for about 3 years.

EXAMPLE 6

A woman, age 63, height 5'5", weight 86.3 kilograms, had a long history of severe varicose veins in her legs, and the right leg had become so swollen that she could scarcely walk.

After about 1 month of treatment with Solution D, her swollen leg returned to normal, and her varicose condition improved as demonstrated by reduced size of the varices. After about 4 years of continuous use of Solution D, no recurrence of her original condition has resulted.

EXAMPLE 7

A man, age 65, height 5'11", weight 77.3 kilograms, had suffered from constipation for many years and had developed hemmorrhoids which bled frequently.

After taking Solution D for about 2 weeks, he began to experience normal bowel movements. His hemorrhoids subsequently became reduced in size. After about 3 years of continued use of Solution D, his bowels function normally. His hemorrhoids have stopped bleeding.

EXAMPLE 8

A man, age 72 at death, height 6', weight 86.4 kilograms, suffered an injury to his leg complicated by an embolus, which apparently had its inception in the leg, moved to the brain, and paralyzed the right side of his body. Subsequently he began to have thrombophlebitis in both his legs.

After use of Solution D was started, his phlebitis gradually disappeared. Beneficial results began to be observed in about two weeks. His hemiparesis did not regress; he continued to be bed ridden. After almost two years of continuously using Solution D, he had not experienced any return of phlebitis to his legs. However this man died from a kidney infection.

EXAMPLE 9

A man, age 77, height 5'8", weight 79.5 kilograms, had severe hypertension for about 20 years which apparently caused him to have seven hemorrhages in his right eye, on successive different occasions. He had tried many antihypertensive medications to no avail. He had been on very strict low salt and low fat diets.

After about two weeks of using Solution D, his blood pressure started to return to normal. After about 4 years of continuous use, his blood pressure has remained normal and no further hemorrhages have been experienced.

EXAMPLE 10

A man, age 67, height 5'10", weight 77.3 kilograms, had severe high blood pressure. He could no longer work, and was quite resigned to die.

After about two weeks of use of Solution D, his mental outlook had improved. Blood pressure gradually returned to normal. Later, the man returned to work and married. After about 4 years of continuous treatment with Solution D, his condition has not deteriorated.

EXAMPLE 11

A man, age 45 height 5'10", weight 70.5 kilograms, had labile high blood pressure for 25 years. When his blood pressure was at its highest point, he had epistaxis. His doctor recommended cauterization of his nose veins to avoid bleeding at night when he was sleeping. Many antihypertension medications were tried with no observed beneficial results.

After commencing treatment with Solution D, he experienced a stabilized and normalized blood pressure apparently within about three weeks. Good health has now been enjoyed for about 2½ years.

EXAMPLE 12

A man, age 77 at death, height 5'9", weight 77.3 kilograms, had gradually deteriorating health. It was felt that he had hypertension atherosclerosis and visceral congestion and also that he had increasing pulmonary insufficiency apparently due to tobacco use. His whole body was swollen and his physicians were treating him with steroids. He was considered to be terminal.

Within two weeks after starting Solution D, his general condition improved. After about three years of continuous use of Solution D, this man continued to be well, except for his pulmonary emphysema which has not improved. (He is now deceased.)

EXAMPLE 13

A man, age 62, height 5'9", weight 86.4 kilograms, had had a previous heart attack. He was found by his physician to have high levels of sugar in his blood and urine. It was felt that he had hypertension, diabetes, and atherosclerosis. His physician prescribed an oral medicine to help stablize his blood sugar. Subsequently, he suffered a second heart attack, and then a third. His condition was critical when solution D was started.

After about 1 and ½ months of consuming the solution, his condition improved. After about 3 years of continuous use of the solution, he has experienced no further heart attacks and his blood sugar levels have decreased. He is ambulatory with restrictions, and his hypertension is controlled.

EXAMPLE 14

A man, age 78, height 5'11", weight 82 kilograms, had mild hypertension, mild arthritis, mild arrythmia, hemorrhoids, dispepsia, cyanotic fingers and toes, mild diabetes, general malaise, and lassitude. After his gall bladder had been removed at age 66, his digestion deteriorated. His diabetes was acquired shortly before treatment with sodium bisulfite began and has been controlled continuously since with diabinese (500 mg daily).

After oral ingestion of aqueous solutions of sodium bisulfite of various concentrates (Solutions A, B, C and D) at dose rates varying from 4 to 20 drops per meal, all of the above identified conditions improved (except for diabetes) within 2–3 months. Thereafter, they gradually disappeared and never recurred. After about seven years of continuous experimental use, the man remains in good health, and is alert and vigorous with excellent color.

After about 3–4 years of use, the man found that he had a prolonged blood clotting time whereupon he reduced his dosage rate somewhat to about 8 drops per meal per day of solution D and his blood clotting time then normalized.

Samples of about 4 cc each of his blood were prepared. To each of these was added about 10 drops of a solution of 10 weight percent sodium bisulfite in distilled water. Each sample was then sealed into a glass vial. After about 2½ years storage at ambient temperatures, these blood samples have not coagulated.

EXAMPLE 15

A widowed woman, age 54, height about 5'5", weight about 60 kilograms, had hypertension, backaches, headaches, and some nervousness. Her blood pressure was 160/110.

After oral consumption of solution D at the rate believed to be about 6 drops per each of three daily meals for about 10 days to 2 weeks, her hypertension began to diminish and after about two months of usage reportedly stabilized at about 120/90. Her backaches, headaches, and depression all disappeared. Use of solution D continues.

EXAMPLE 16

A woman, age 62, height about 5'7", weight about 62 kilograms had hypertension for 10 years with symptoms which included shortness of breath especially when walking, getting red in the face, headaches, dizzyness, and inability to exercise. Her blood pressure was 190/130.

After oral consumption of solution D at the rate believed to be about 6 drops per each of three daily meals, her blood pressure was reduced to 160/90. Between the second and third months of use of solution D, all above symptoms went away. Use of solution D continues.

EXAMPLE 17

A woman, age 86 years, had hypertension. Her blood pressure was 200/120.

After use of solution D at the dose rate believed to be about 6 drops per each of three daily meals, her blood pressure fell to a value in the range from about 160–170 to 90–100 and is being maintained at these reduced values through continued use of solution D.

EXAMPLE 18

A woman, age about 45 years, had hypertension. Her blood pressure was 190/110.

After use of solution D at the dose rate believed to be about 7 drops per each of three daily meals, her blood pressure fell to about 150/90 within about 10 days. Thereafter, use of agent D was discontinued.

EXAMPLE 19

A hypertensive human, about 60 years of age had a blood pressure of about 170/110.

After 7 to 8 days of oral consumption of solution D at the rate believed to be about 7 drops per each of three daily meals, the patients blood pressure was reduced to 160/90. On the 10th day, a slight rise in blood pressure was observed. Use of solution D was then discontinued.

EXAMPLE 20

A woman, about 68 years old, had had hypertension all her life. She was strongly claustrophobic. Also, she had varicose veins. Her blood pressure was 170/100.

After use of solution D for 6 months at the rate believed to be about 14 to 21 drops per day (about seven drops for each of her daily meals), her blood pressure was reduced to 136/86. Use of solution D continues.

EXAMPLE 21

A man, age 44, weight 82 kilograms, had had hypertension. His blood pressure was 170/120, sometimes 160/110.

After consumption of solution D for about 3 months at the rate of about 7 drops per meal per day (man eats 2 meals per day) for about 3 months, his blood pressure dropped to from about 140/110 to 140/90. The man, by opthalmological examination, was found to have grade 2 eye grounds.

The man at one point discontinued use of solution D. Within two weeks his blood pressure increased. He started using solution D again at the same dose rate and his blood pressure again was reduced to the values above given.

EXAMPLE 22

A man, age 70 weight 64 kilograms, had had hypertension for four years. Three years ago he had had a neck hematoma (in back of one ear) and an embolus in the brain. He experienced no physical residuals but can now speak only slowly and has poor sensibility in his fingers (three have no sensitivity to touch). His blood pressure was 195/100.

After about one year of using solution D at the rate of 6 drops per each of 3 daily meals, his blood pressure was reduced to about 145/90. Use of solution D continues.

EXAMPLE 23

A man, age 43, weight 74 kilograms, had had hypertension for 15 years. His blood pressure rises occasionally to 180/110.

After about two and one half years of using solution D first at the rate of 15 drops per day and now at the rate of about 14 drops per day for 6 months, his blood pressure was found to be about 170/100 and at times is 140/87. Opthalmoscopic examination reveals normal eyes. Use of solution D continues.

EXAMPLE 24

A man, age 47 weight 93 kilograms had hypertension and a blood pressure of 160/100.

After using solution D for about 2 months at the rate of about 10 drops per each of 3 daily meals, his blood pressure was 125/85.

After a further period of use, the man discontinued use of solution D within 9 days, his ears began to buzz and his blood pressure went up in about 8 days. He started use of solution D again at the same dosage rate and his blood pressure again dropped. Currently, his blood pressure was found to be about 140/106. Use of solution D continues.

What is claimed is:

1. A process for achieving improvement in hypertension in a human suffering from said condition comprising orally introducing into said human sodium bisulfite as an aqueous solution at the rate of from about 0.2 to 2.0 mgm of sodium bisulfite per kilogram of body weight per 24 hours.

2. A process for achieving improvement of hypertension comprising orally feeding a human afflicted with said disease a pharmacologically effective amount of a compound selected from the group consisting of sodium bisulfite and sodium metabisulfite at the rate of from about 0.2 to 2.0 mgm of such compound per kilogram of said human's body weight per day.

* * * * *